United States Patent [19]

Boardman et al.

[11] Patent Number: 4,916,169

[45] Date of Patent: Apr. 10, 1990

[54] VISIBLE RADIATION ACTIVATED HYDROSILATION REACTION

[75] Inventors: Larry D. Boardman; Joel D. Oxman, both of St. Paul, Minn.

[73] Assignee: Minnesota Mining and Manufacturing Company, St. Paul, Minn.

[21] Appl. No.: 242,478

[22] Filed: Sep. 9, 1988

[51] Int. Cl.$^4$ ................................................ C08F 2/46
[52] U.S. Cl. .......................................... 522/27; 528/15; 522/26; 522/29; 522/48; 522/49; 522/53; 522/67; 522/69; 522/99; 522/104; 522/110; 522/172
[58] Field of Search .............. 522/26, 27, 29, 48, 522/49, 53, 67, 69, 99, 104, 110, 172; 528/15

[56] References Cited

U.S. PATENT DOCUMENTS

| | | | |
|---|---|---|---|
| 3,159,662 | 12/1964 | Ashby | 260/448.2 |
| 3,178,464 | 4/1965 | Pierpoint | 260/448.2 |
| 3,220,972 | 11/1965 | Lamoreaux | 260/46.5 |
| 3,313,773 | 4/1967 | Lamoreaux | 260/46.5 |
| 3,410,886 | 11/1968 | Joy | 260/448.2 |
| 3,470,225 | 9/1969 | Knorre | 260/448.2 |
| 3,567,755 | 3/1971 | Seyfried | 260/448.2 |
| 3,814,731 | 6/1974 | Nitzsche | 260/46.5 |
| 4,243,718 | 1/1981 | Murai et al. | 428/411 |
| 4,276,252 | 6/1981 | Kreis et al. | 264/222 |
| 4,288,345 | 9/1981 | Ashby et al. | 252/431 R |
| 4,510,094 | 4/1985 | Drahnak | 260/429 CY |
| 4,530,879 | 6/1985 | Drahnak | 428/352 |
| 4,603,168 | 7/1986 | Sasaki et al. | 522/29 |
| 4,603,215 | 7/1986 | Chandra et al. | 556/136 |
| 4,640,939 | 2/1987 | Cavezzan et al. | 522/99 |
| 4,670,531 | 6/1987 | Eckberg | 528/15 |
| 4,699,813 | 10/1987 | Cavezzan | 427/387 |
| 4,705,765 | 11/1987 | Lewis | 502/152 |
| 4,712,092 | 12/1987 | Boldridge, Jr. et al. | 340/365 A |

FOREIGN PATENT DOCUMENTS 0238033 9/1987 European Pat. Off. .

*Primary Examiner*—Melvyn I. Marquis
*Attorney, Agent, or Firm*—Donald M. Sell; Walter N. Kirn; David L. Weinstein

[57] ABSTRACT

A process for the addition of compounds containing silicon-bonded hydrogen to compounds containing aliphatic unsaturation and compositions suitable for said process. The process is activated by visible radiation and is conducted in the presence of a platinum complex having one cyclopentadienyl group that is eta-bonded to the platinum atom and three aliphatic groups that are sigma-bonded to the platinum atom and a sensitizer that is capable of absorbing visible light and is capable of transferring energy to said platinum complex such that the hydrosilation reaction is initiated upon exposure to visible light. The invention also provides for use in the aforementioned process.

27 Claims, No Drawings

VISIBLE RADIATION ACTIVATED HYDROSILATION REACTION

BACKGROUND OF THE INVENTION

1. Field of the Invention

This invention relates to a hydrosilation process involving the reaction of a compound containing silicon-bonded hydrogen with a compound containing aliphatic unsaturation in the presence of visible radiation, and to compositions which contain a visible radiation-sensitive sensitizer that is useful in said process. The invention further relates to polysiloxane compositions, prepared by said process, which compositions are useful for preparing dental impressions, adhesives, release liners, and caulking materials.

2. Discussion of the Art

Numerous patents teach the use of various complexes of cobalt, rhodium, nickel, palladium, or platinum as catalysts for accelerating the thermally-activated addition reaction (hydrosilation) between a compound containing silicon-bonded hydrogen and a compound containing aliphatic unsaturation. For example, U.S. Pat. No. 4,288,345 (Ashby, et al) discloses as a catalyst for hydrosilation reactions a platinum-siloxane complex. U.S. Pat. No. 3,470,225 (Knorre, et al) discloses production of organic silicon compounds by addition of a compound containing at least one non-aromatic double or triple carbon-to-carbon bond using a platinum compound of the empirical formula $PtX_2(RCOCR'COR'')_2$ wherein X is halogen, R is alkyl, R' is hydrogen or alkyl, and R'' is alkyl or alkoxy. The catalysts disclosed in the foregoing patents are characterized by their high catalytic activity. Other platinum complexes for accelerating the aforementioned thermally-activated addition reaction include: a platinum-cyclobutane complex having the formula $(PtCl_2\text{---}C_3H_6)_2$ (U.S. Pat. No. 3,159,662, Ashby); a complex of a platinous salt and an olefin (U.S. Pat. No. 3,178,464, Pierpoint); a platinum-containing complex prepared by reacting chloroplatinic acid with an alcohol, ether, aldehyde, or mixtures thereof (U.S. Pat. No. 3,220,972, Lamoreaux); a platinum compound selected from trimethylplatinum iodide and hexamethyldiplatinum (U.S. Pat. No. 3,313,773, Lamoreaux); a hydrocarbyl or halohydrocarbyl nitrile-platinum (II) halide complex (U.S. Pat. No. 3,410,886, Joy); a hexamethyl-dipyridine-diplatinum iodide (U.S. Pat. No. 3,567,755, Seyfried, et al); a platinum curing catalyst obtained from the reaction of chloroplatinic acid and a ketone having up to 15 carbon atoms (U.S. Pat. No. 3,814,731, Nitzsche, et al); a platinum compound having the general formula $(R')PtX_2$ where R' is a cyclic hydrocarbon radical or substituted cyclic hydrocarbon radical having two aliphatic carbon-carbon double bonds, and X is a halogen or alkyl radical (U.S. Pat. No. 4,276,252, Kreis, et al); platinum alkyne complexes (U.S. Pat. No. 4,603,215, Chandra et al.); platinum alkenylcyclohexene complexes (U.S. Pat. No. 4,699,813, Cavezzan); and a colloidal hydrosilation catalyst provided by the reaction between a silicon hydride or a siloxane hydride and a platinum (0) or platinum (II) complex (U.S. Pat. No. 4,705,765, Lewis). Although these platinum complexes and many others are useful as catalysts in processes for accelerating the thermally-activated addition reaction between the compounds containing silicon-bonded hydrogen and compounds containing aliphatic unsaturation, processes for promoting the visible radiation activated addition reaction between these compounds are unknown. Platinum complexes that can be used to initiate ultraviolet radiation activated hydrosilation reactions have also been disclosed, e.g., platinum azo complexes (U.S. Pat. No. 4,670,531, Eckberg); ($\eta^4$-cyclooctadiene)diarylplatinum complexes (U.S. Pat. No. 4,530,879, Drahnak); and ($\eta^5$-cyclopentadienyl)trialkylplatinum complexes (U.S. Pat. No. 4,510,094, Drahnak). Other compositions that are curable by ultraviolet radiation include those described in U.S. Pat. Nos. 4,640,939 and 4,712,092 and in European patent application No. 0238033. However, these patents do not indicate that the platinum complexes disclosed therein would be useful for initiating the visible radiation activated hydrosilation reaction.

SUMMARY OF THE INVENTION

In one aspect, this invention provides an improved process for the visible radiation-activated addition reaction of a compound containing silicon-bonded hydrogen with a compound containing aliphatic unsaturation, said addition being referred to as hydrosilation, the improvement comprising using, as a platinum hydrosilation catalyst, an ($\eta^5$-cyclopentadienyl)tri($\sigma$-aliphatic)-platinum complex, and, as a sensitizer, a compound that absorbs visible light, i.e., light having a wavelength ranging from about 400 nm to about 800 nm and that is capable of transferring energy to the aforementioned platinum complex such that the hydrosilation reaction is initiated upon exposure to visible light. The process is applicable both to the synthesis of low molecular weight compounds and to the curing of high molecular weight compounds, i.e. polymers, containing unsaturated groups, e.g., —C≡C—. For example, the process comprises exposing to visible radiation, i.e., radiation having a wavelength of about 400 nm to about 800 nm, a composition capable of undergoing hydrosilation comprising (a)

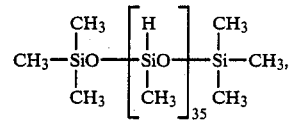

(b)

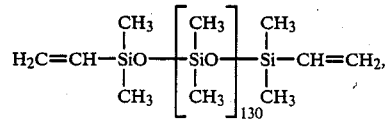

(c) a platinum complex catalyst having one cyclopentadienyl group that is eta-bonded to the platinum atom and three aliphatic groups that are sigma-bonded to the platinum atom, and (d) a sensitizer capable of absorbing actinic radiation having a wavelength of about 400 nm to about 800 nm, and having a triplet energy of at least 31 Kcal/mole.

The invention further involves novel compositions, capable of undergoing hydrosilation, containing both the aforementioned platinum complex and the aforementioned sensitizer.

An important application of the process and compositions of the invention is as a visible light curable impression material for dental applications.

Advantages of the platinum complex and sensitizer in accelerating the visible radiation-activated addition reaction of compounds containing silicon-bonded hydrogen with compounds containing aliphatic unsaturation include the following:

(1) the reaction composition will not react prematurely or readily in the absence of visible radiation;
(2) since heat is not required, the addition reaction can be carried out on the surface of a heat-sensitive substrate without adversely affecting the substrate;
(3) visible light radiation curing requires less energy than does either ultraviolet curing or thermal curing; and
(4) the use of visible radiation provides greater safety than does the use of ultraviolet radiation.

DETAILED DESCRIPTION

As used in this application, the term "compound", unless indicated otherwise, is a chemical substance which has a particular molecular identity or is made of a mixture of such substances, e.g. polymeric substances. The term "hydrosilation" means the addition of organosilicon compounds containing silicon-bonded hydrogen to a compound containing an aliphatic multiple bond, and in the hydrosilation process described in this application, it refers to those processes in which platinum-containing catalysts are used to effect the addition of an organosilicon compound having a silicon-bonded hydrogen atom to an aliphatically unsaturated compound having either olefinic or acetylenic unsaturation.

In a preferred embodiment of the invention, the platinum complex is an ($\eta^5$-cyclopentadienyl)tri($\sigma$-aliphatic)platinum complex having the formula

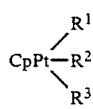    I wherein
Cp represents a cyclopentadienyl group that is eta-bonded to the platinum atom, the cyclopentadienyl group being unsubstituted or substituted by one or more groups that do not interfere in a hydrosilation reaction, and
each of $R^1$, $R^2$, and $R^3$ represents an aliphatic group having from one to eighteen carbon atoms, said $R^1$, $R^2$, and $R^3$ groups being sigma-bonded to the platinum atom.

The groups represented by $R^1$, $R^2$, and $R^3$ can be unsubstituted or substituted hydrocarbyl groups, or unsubstituted or substituted acyl groups, said substituents, if any, not interfering in a hydrosilation reaction. The groups can be straight-chain, branched-chain, and, if sufficiently large, cyclic.

($\eta^5$-Cyclopentadienyl)trimethylplatinum can be prepared by the addition of a solution of cyclopentadienylsodium in tetrahydrofuran to an equimolar amount of trimethylplatinum iodide dissolved in benzene, and isolation of the product complex from the filtrate, according to the procedure of S. D. Robinson and B. L. Shaw, J. Chem. Soc. 1965, 1529. Other ($\eta^5$-cyclopentadienyl)-trialiphaticplatinum complexes can be prepared by using corresponding amounts of substituted cyclopentadienylsodium in place of cyclopentadienylsodium and various trialiphatic platinum halides in place of trimethylplatinum iodide.

Representative examples of suitable ($\eta^5$-cyclopentadienyl)trialiphaticplatinum complexes useful in the practice of this invention include the following, in which (Cp) represents the ($\eta^5$-cyclopentadienyl) group:
(Cp)trimethylplatinum
(Cp)ethyldimethylplatinum
(Cp)triethylplatinum
(Cp)triallylplatinum
(Cp)tripentylplatinum
(Cp)trihexylplatinum
(methyl-Cp)trimethylplatinum
(trimethylsilyl-Cp)trimethylplatinum
(dimethylphenylsilyl-Cp)trimethylplatinum
(Cp)acetyldimethylplatinum
Other suitable ($\eta^5$-cyclopentadienyl)trialiphaticplatinum complexes suitable for this invention are described in U.S. Pat. No. 4,510,094, incorporated herein by reference.

Sensitizers suitable for this invention are those compounds capable of absorbing actinic radiation within the visible region of the electromagnetic spectrum, i.e., about 400 nm to about 800 nm, and capable of transferring energy to the platinum complex. It has been discovered that they must have a triplet energy level of at least 31 Kcal/mole, and must not inhibit the hydrosilation reaction. Sensitizers are preferably selected from two classes of compounds: (1) polycyclic aromatic compounds and (2) aromatic compounds containing a ketone chromophore. The sensitizer compounds can be substituted with any substituent that does not interfere with the light absorbing and energy transferring capabilities of the sensitizer compound or the hydrosilation catalyst. Examples of typical substituents include alkyl, alkoxy, aryl, aryloxy, aralkyl, alkaryl, halogen, etc. Representative examples of polycyclic aromatic sensitizers suitable for the invention include anthracene, 9-vinylanthracene, 9,10-dimethylanthracene, 9,10-dichloroanthracene, 9,10-dibromoanthracene, 9,10-diethylanthracene, 9,10-diethoxyanthracene, 2-ethyl-9,10-dimethylanthracene, naphthacene, pentacene, benz[a]anthracene, 7,12-dimethylbenz[a]anthracene, azulene and the like.

Some of the foregoing examples are illustrated below:

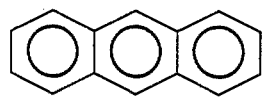

anthracene

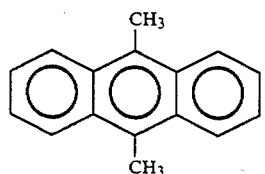

9,10-dimethylanthracene

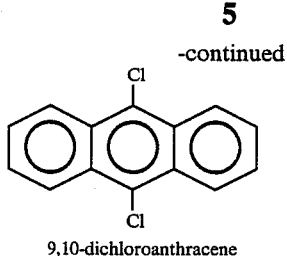

9,10-dichloroanthracene

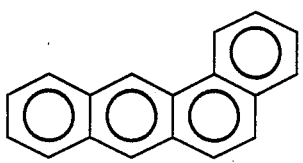

benz[a]anthracene

Representative examples of aromatic ketone sensitizers suitable for this invention include 2-chlorothioxanthone, 2-isopropylthioxanthone, thioxanthone, anthraquinone, benzophenone, 1-chloroanthraquinone, bianthrone, and the like. Some of the foregoing examples are illustrated below:

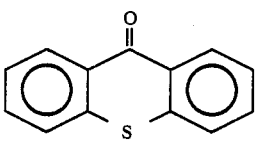

thioxanthone

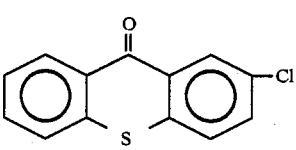

2-chlorothioxanthone

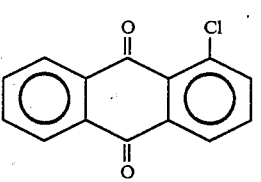

1-chloroanthraquinone

Turning now to the reactants to be used in the radiation-activated addition reaction, compounds containing aliphatic unsaturation which are useful in the present invention have olefinic or acetylenic unsaturation. These compounds are well-known in the art of hydrosilation and are disclosed in such patents as U.S. Pat. No. 3,159,662 (Ashby), U.S. Pat. No. 3,220,972 (Lamoreaux), and U.S. Pat. No. 3,410,886 (Joy), which disclosures of said compounds are incorporated herein. In instances where these unsaturated compounds contain elements other than carbon and hydrogen, it is preferred that these elements be either oxygen, nitrogen, silicon, a halogen, or a combination thereof. The aliphatically unsaturated compound can contain one or more carbon-to-carbon multiple bonds. Representative examples of the aliphatically unsaturated hydrocarbons which can be employed include mono-olefins, for example, ethylene, propylene, and 2-pentene, diolefins, for example, divinylbenzene, butadiene, and 1,5-hexadiene, cycloolefins, for example, cyclohexene and cycloheptene, and monoalkynes, for example, acetylene, propyne, and 1-butene-3-yne. The aliphatically unsaturated compounds can have up to 20 to 30 carbon atoms, or more.

Oxygen-containing aliphatically unsaturated compounds can also be used, especially where the unsaturation is ethylenic, such as methylvinyl ether, divinylether, phenylvinyl ether, monoallyl ether of ethylene glycol, allyl aldehyde, methylvinyl ketone, phenylvinyl ketone, acrylic acid, methacrylic acid, methyl acrylate, allyl acrylate, methyl methacrylate, allyl methacrylate, vinylacetic acid, vinyl acetate, and linolenic acid. Heterocyclic compounds containing aliphatic unsaturation in the ring, such as dihydrofuran, and dihydropyran, are also suitable for the present invention.

Halogenated derivatives of the previously mentioned aliphatically unsaturated compounds can be employed, including acyl chlorides as well as compounds containing a halogen substituent on a carbon atom other than a carbonyl carbon atom. Such halogen-containing compounds include, for example, vinyl chloride, and the vinylchlorophenyl esters.

Unsaturated compounds containing nitrogen substituents such as acrylonitrile, N-vinylpyrrolidone alkyl cyanide, nitroethylene, etc., are also useful in the practice of the present invention.

Other unsaturated compounds useful in the practice of the present invention include polymers containing aliphatic unsaturation, such as the polyester resins prepared from polybasic saturated or unsaturated acids with polyhydric unsaturated alcohols, and the polyester resins prepared by reacting unsaturated polybasic acids with saturated polyhydric alcohols.

A particularly useful type of unsaturated compound which can be employed in the practice of the present invention is that containing silicon, such as those compounds commonly referred to as organosilicon monomers or polymers. These unsaturated organosilicon compounds have at least one aliphatically unsaturated organic radical attached to silicon per molecule. The aliphatically unsaturated organosilicon compounds include silanes, polysilanes, siloxanes, silazanes, as well as monomeric or polymeric materials containing silicon atoms joined together by methylene or polymethylene groups or by phenylene groups.

Preferred among the aliphatically unsaturated organosilicon compounds useful in the present invention are the monomeric silanes having the empirical formula $$R_b^4 R_c^5 SiX_{(4-b-c)} \qquad II$$

the cyclopolysiloxanes having the empirical formula $$(R^4 R^5 SiO)_d \qquad III$$

and the polyorganosiloxanes having the empirical formula $$R_e^4 R_f^5 SiO_{(4-e-f)/2} \qquad IV$$

wherein
$R^4$ represents a monovalent aliphatic unsaturated hydrocarbyl group,
$R^5$ represents a monovalent saturated hydrocarbyl group,
X represents a hydrolyzable group,
b is an integer from 1 to 4, inclusive, c is zero or an integer from 1 to 3, inclusive, the sum of b and c being 1 to 4, d is an integer from 3 to 18, inclusive, e is a number having a value of 0.0001 to 1, inclusive, and f is zero or a number such that the sum of e and f is equal to 1 to 2, inclusive.

Monovalent aliphatic unsaturated hydrocarbyl groups represented by $R^4$ include alkenyl, for example, vinyl, propenyl, isopropenyl, 3-butenyl, and 5-hexenyl. Groups represented by $R^5$ include, for example, alkyl groups, such as methyl, ethyl, and pentyl; cycloalkyl groups, such as cyclopentyl and cyclohexyl; aryl groups such as phenyl and tolyl; aralkyl groups, such as benzyl and phenylethyl; halogenated hydrocarbyl groups, such as haloalkyl, e.g., chloromethyl, trichloromethyl, and 3,3,3-trifluoropropyl, and haloaryl, e.g., chlorophenyl. Hydrolyzable groups represented by X include, for example, halogen groups such as chloro, bromo, and iodo, alkoxy groups such as methoxy, ethoxy, and phenoxy, and acyloxy groups such as acetoxy, propionoxy, and benzoyloxy. A hydrolyzable group is one which undergoes a displacement reaction with water.

In one particularly preferred embodiment of the process of the invention, the compound containing aliphatic unsaturation is an aliphatically unsaturated polyorganosiloxane represented by the general formula:

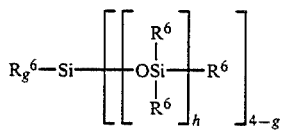

wherein each $R^6$ can be the same or different and represents a non-halogenated or halogenated ethylenically-unsaturated group having from 2 to 18 carbon atoms, such as vinyl, propenyl, and chlorovinyl, a non-halogenated or halogenated alkyl group having from 1 to 18 carbon atoms, such as methyl, ethyl, propyl, hexyl, octyl, dodecyl, octadecyl, trichloromethyl, and 3,3,3-trifluoropropyl, a non-halogenated or halogenated cycloalkyl group having from 3 to 12 carbon atoms, such as cyclopentyl and cyclohexyl, or phenyl, at least 70% of all $R^6$ groups being methyl groups, but no more than 10% of all $R^6$ groups being vinyl or other alkenyl, e.g., having 3 to 18 carbon atoms, and at least one of the $R^6$ groups being vinyl or other alkenyl, e.g., having 3 to 18 carbon atoms;

h is a number having a value from 1 to about 3000;

g is 0, 1, 2, or 3.

The reactant containing the silicon-hydrogen linkage can be a polymeric compound or a compound that is not polymeric. These compounds are well-known in the art and are disclosed in the patents which describe the aliphatically unsaturated reactant, i.e., Ashby, U.S. Pat. No. 3,159,662; Lamoreaux, U.S. Pat. No. 3,220,972; and Joy, U.S. Pat. No. 3,410,886. The reactant containing the silicon-hydrogen linkage should contain at least one silicon-bonded hydrogen atom per molecule, with no more than three hydrogen atoms attached to any one silicon atom.

Some classes of compounds having a silicon-bonded hydrogen atom which can be used in the invention are organosilanes having the empirical formula $$(H)_jSi(R^7)_k(X)_{(4-j-k)} \qquad VI$$

organocyclopolysiloxanes having the empirical formula $$(HR^7SiO)_d \qquad VII$$

and organohydrosiloxane polymers or copolymers having the empirical formula $$(R^7)_fSi(H)_eO_{(4-e-f)/2} \qquad VIII$$

wherein $R^7$ represents an organic group, preferably selected from the group consisting of monovalent hydrocarbyl groups, and halogenated monovalent hydrocarbyl groups, j is the integer 1, 2, or 3, k is zero or an integer of 1 to 3, inclusive, the sum of j and k being equal to 1 to 4, X, d, e and f are as defined above for formulas II, III, and IV.

Among the groups represented by $R^7$ include, for example, alkyl groups having 1 to 18 carbon atoms, e.g., methyl, ethyl, propyl, octyl, and octadecyl, cycloalkyl groups having 5 to 7 ring carbon atoms, e.g., cyclohexyl and cycloheptyl, aryl groups having 6 to 18 carbon atoms, e.g., phenyl, naphthyl, tolyl, xylyl, and combinations of alkyl and aryl groups, e.g., aralkyl groups, such as, benzyl and phenylethyl, and halo-substituted groups thereof; e.g., chloromethyl, chlorophenyl, and dibromophenyl. Preferably, the $R^7$ group is methyl or both methyl and phenyl. The $R^7$ group can also be an unsaturated aliphatic group having 1 to 20 carbon atoms, such as alkenyl or cycloalkenyl, e.g., vinyl, allyl and cyclohexenyl. When the $R^7$ group is a group with aliphatic unsaturation, the silicon compound containing silicon-hydrogen linkages can be reacted with itself to form a polymer.

Among the inorganic compounds which contain silicon-bonded hydrogen atoms and which are useful as reactants in the process of the present invention are included, for example, trichlorosilane, dibromosilane, pentachlorodisilane, pentachlorodisiloxane, and heptachlorotrisilane.

A preferred compound having silicon-bonded hydrogen useful in this invention is a polyorganohydrosiloxane having the general formula:

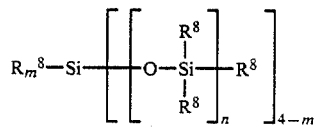

wherein each $R^8$ can be the same or different and represents hydrogen, an alkyl group having 1 to 18 carbon atoms, a cycloalkyl group having 3 to 12 carbon atoms, or a phenyl group, at least one but not more than one-half of all the $R^8$ groups in the siloxane being hydrogen;

m is 0, 1, 2, or 3; and n is a number having an average value from 1 to about 3000.

The hydrosilation composition useful in the synthesis of low molecular weight compounds by the process of the invention can be prepared by mixing about 0.1 to about 10.0 equivalent weights of the compound having silicon-bonded hydrogen with one equivalent weight of the compound having aliphatic unsaturation and then adding an amount of platinum complex catalyst sufficient to catalyze the reaction and an amount of sensitizer sufficient to sensitize the platinum complex upon exposure to actinic radiation having a wavelength from about 400 nm to about 800 nm. The amount of the catalyst can range from about 5 to about 1000 parts by weight, preferably from about 50 to about 500 parts by weight, per 1,000,000 parts by weight of the total composition. The amount of sensitizer can range from about 50 to about 50,000 parts by weight, preferably from about 500 to about 5000 parts by weight, per 1,000,000 parts by weight of total composition.

Known techniques can be used to conduct the hydrosilation reaction. In carrying out a hydrosilation reaction in the practice of this invention, the reactants and catalyst can be introduced into a vessel equipped for stirring, where the mixture is stirred until it is homogenous. If either of the reactants is a solid or is extremely viscous, a solvent can be introduced into the vessel to facilitate uniform mixing of the reactants. Suitable solvents include aromatic hydrocarbons, such as xylene and toluene, aliphatic hydrocarbons, such as hexane and mineral spirits, and halogenated hydrocarbons, such as chlorobenzene and trichloroethane. It is desirable that the solvent be transmissive to visible radiation. From about 0.1 to about 10 parts of solvent per part by weight of the combined reactants may be used. The resulting reaction product will generally be sufficiently pure for its intended use. However, it may be desirable to remove the solvent if one has been employed.

The hydrosilation compositions useful in the preparation of higher molecular weight cured siloxane polymers, by the process of this invention, can be prepared by mixing an aliphatically unsaturated polysiloxane and the compound having silicon-bonded hydrogen in such a proportion so as to provide about 0.1 to about 10.0 silicon-bonded hydrogen atoms per unsaturated group, and then adding from about 5 to about 1000 parts by weight, preferably from about 50 to about 500 parts by weight of platinum complex catalyst and from about 50 to about 50,000 parts by weight, preferably from about 500 to about 5000 parts by weight of sensitizer, per 1,000,000 parts by weight of the total composition. The reaction mixture can be mixed, as by stirring, blending, or tumbling, until it is homogenous.

The thoroughly mixed composition can then be applied to a substrate by any suitable means, such as by spraying, dipping, knife coating, curtain coating, roll coating, or the like, and the coating cured by using conventional techniques for providing visible radiation. It is preferred that curing be conducted by exposing the coated substrate to radiation having a wavelength of about 400 nm to about 800 nm. Depending on the particular silicone formulation, catalyst, sensitizer and intensity of the visible radiation, curing can be accomplished in a period from less than one second to less than 30 minutes. Any radiation source emitting radiation above about 400 nm can be used. Examples of suitable radiation sources include tungsten halogen lamps, xenon arc lamps, mercury arc lamps, incandescent lamps, and fluorescent lamps. Particularly preferred sources of visible radiation are tungsten halogen, xenon arc, and mercury arc lamps.

Various additives conventionally included in hydrosilation compositions can be included in the curable compositions, depending on the intended purpose of the composition. Fillers and/or pigments, such as chopped fibers, crushed polymers, talc, clay, titanium dioxide, and fumed silica can be added. Soluble dyes, oxidation inhibitors, and/or any material that does not interfere with the catalytic activity of the platinum complex and does not absorb visible light radiation at the absorption wavelength of the sensitizer can be added to the composition.

The shelf life of the curable compositions containing the catalyst and sensitizer can be extended by the addition of a conventional catalyst inhibitor. The amount of catalyst inhibitor can vary from about 1 to about 10 times, or more, the amount of platinum complex, depending on the activity of the particular complex or complex-accelerator used and the shelf life desired for the composition. Greater amounts of inhibitor should be used with the more active complexes, with lesser amounts being used for the less active complexes. Hydrosilation inhibitors are well known in the art and include such compounds as acetylenic alcohols, certain polyolefinic siloxanes, pyridine, acrylonitrile, organic phosphines and phosphites, unsaturated amides, and alkyl maleates.

The hydrosilation compositions of this invention can be applied to the surface of any solid substrate for a variety of purposes. Examples of such substrates include paper, cardboard, wood, cork, plastic such as polyester, nylon, polycarbonate, etc., woven and nonwoven fabric such as cotton, polyester, nylon, etc., metal, glass, and ceramic.

It is often advantageous to prime the surface of nonporous substrates to which the hydrosilation composition is to be applied to improve the adhesion of the composition to the substrate. Many primers and priming techniques (e.g., corona treatment) are described in the art and should be chosen on the basis of the substrate to be used. For example, the epoxy-functional siloxanes as taught in U.S. Pat. No. 4,243,718 (Murai, et al) are useful for priming the surface of plastic films such as polyester and polyvinylchloride.

Compositions of this invention can be applied and cured in relatively thick sections, such as an impression material for dental applications or a fast-setting caulking material.

Advantages of this invention are further illustrated by the following examples, where the parts referred to are parts by weight. The particular materials and amounts recited as well as other conditions and details given should not be construed to unduly limit this invention.

Compositions of this invention were evaluated for cure speed in the following manner.

Molds made from a 1.5 mm thick "Teflon" sheet with a 6 mm diameter hole through the sheet were clamped to clean glass slides so that the central axis of the hole in the mold was normal to the glass slide. The hole was filled with a sample of the composition being evaluated. A "Visilux" 2 dental curing light (available from Minnesota Mining and Manufacturing Company) with a light output wavelength between 400 and 500 nm was clamped to a ring stand and positioned such that the cylindrical tip of the light source was 5.0 mm above the top of the "Teflon" mold. The center of the 6 mm diameter sample was directly beneath the light tip. The sample was irradiated with the "Visilux" 2 light until a tack-free, cohesive silicone polymer was obtained as determined with a metal probe. All samples were tested in duplicate or triplicate.

EXAMPLES 1–14

A stock composition was prepared by mixing in a glass container 94.86 parts by weight of vinyl terminated polysiloxane polymer having the formula:

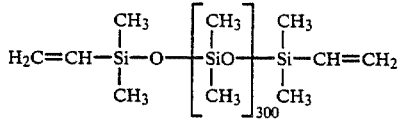

and 4.99 parts by weight of a compound containing silicon-bonded hydrogen atoms having the formula

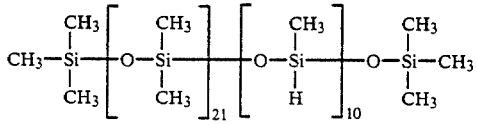

and 0.15 parts by weight of (Cp)trimethylplatinum. To each 2 g portion of the stock composition in glass vials was added 2 mg of one of the sensitizers listed in Table I, and the contents of each vial thoroughly mixed with slight heating.

TABLE I

| Example no. | Sensitizer | Gel time (seconds) |
|---|---|---|
| Comp.A* | None | 117 |
| 1 | perylene | 118 |
| 2 | anthracene | 105 |
| 3 | 9,10-dibromoanthracene | 92 |
| 4 | benzo[a]pyrene | 61 |
| 5 | 9,10-diethoxyanthracene | 60 |
| 6 | 2-ethyl-9,10-dimethylanthracene | 48 |
| 7 | 9,10-dichloroanthracene | 45 |
| 8 | 9,10-dimethylanthracene | 43 |
| 9 | anthraquinone | 113 |
| 10 | bianthrone | 107 |
| 11 | 1-chloroanthraquinone | 80 |
| 12 | 2-chlorothioxanthone | 33 |
| 13 | benzil | Air Inhibition |
| 14 | camphorquinone | Air Inhibition |

The data of Table I show that several sensitizer compounds are capable of increasing the cure speed of the said silicone formulations compared to Comparative Example A, which contained no sensitizer compound. Cure speed was enhanced as much as 3.5 times in the case of 2-chlorothioxanthone relative to the control.

EXAMPLES 15–23

The procedure of Example 1 was repeated with the exceptions that in place of the vinyl terminated polysiloxane of Examples 1–14, was used 97.5 parts by weight of a vinyl-terminated polysiloxane having the formula:

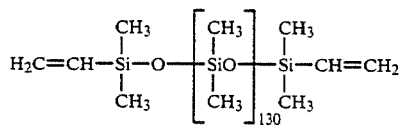

and 2.5 parts by weight of a silicon-bonded hydrogen compound (available as DC 1107 from Dow Corning Corporation) having the formula:

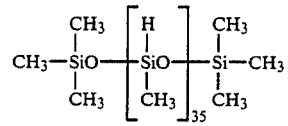

Platinum in the form of (Cp)trimethylplatinum complex was added to the formulation at a concentration of 50 parts per million. Table II summarizes the gel times observed upon addition of 0.02 percent by weight of various sensitizer compounds.

TABLE II

| | Sensitizer | Gel time (seconds) |
|---|---|---|
| Comp. B | None | 130 |
| 15 | pyrene | 140 |
| 16 | perylene | 130 |
| 17 | tetracene | 125 |
| 18 | 9,10-dichloroanthracene | 65 |
| 19 | 9,10-dimethylanthracene | 60 |
| 20 | 2-chlorothioxanthone | 50 |
| 21 | 4-phenylbenzophenone | 150 |
| 22 | 4-chlorobenzophenone | 140 |
| 23 | 2,7-dichlorofluorenone | 120 |

The data of Table II further show that the cure speed of silicone compositions can be significantly enhanced in the presence of visible light absorbing sensitizers.

EXAMPLE 24

A stock composition was prepared by mixing in a container 94.90 parts by weight of the vinyl terminated polysiloxane described in Example 1 and 5.00 parts by weight of the silicon-bonded hydrogen compound described in Example 1. To the formulation was added 0.10 part by weight of 9,10-dimethylanthracene sensitizer and the resulting mixture was mixed thoroughly with gentle heating. Samples (2 g) were prepared from the stock formulation by addition of (Cp)trimethylplatinum in the range of 0 to 0.45 percent by weight of the final composition. Samples were tested for gel time upon exposure to light as described in Example 1 and results recorded in Table III.

TABLE III

| Sample | Wt. percent CpPt (CH$_3$)$_3$ | ppm Pt | Gel time (seconds) |
|---|---|---|---|
| 1* | 0.15 | 960 | 117 |
| 2 | 0.00 | 0 | did not cure |
| 3 | 0.05 | 320 | 57 |
| 4 | 0.15 | 960 | 47 |
| 5 | 0.30 | 1920 | 33 |
| 6 | 0.45 | 2880 | 32 |

*No sensitizer was used in this sample.

The data of Table III show that in the absence of Pt no cure of the composition occurs. The data in Table III also show cure speed is increasingly enhanced by further addition of (Cp)trimethylplatinum up to about 2000 ppm platinum. Further addition of platinum is not beneficial.

EXAMPLE 25

The procedure of Example 1 was repeated with the exception that 2-ethyl-9,10-dimethylanthracene (EDMA) was used as the sensitizer in a concentration range of 0.0 to 0.15 parts by weight of the total composition. Table IV summarizes the gel times for several silicone formulations that vary as a function of EDMA concentration.

TABLE IV

| Sample | EDMA Sensitizer | Gel time (seconds) |
|---|---|---|
| 1 | 0.0 | 121 |
| 2 | 0.02 | 77 |
| 3 | 0.04 | 57 |
| 4 | 0.06 | 52 |
| 5 | 0.10 | 39 |
| 6 | 0.15 | 37 |

The data in Table IV show that for a constant platinum concentration, gel time decreases as a function of increasing sensitizer concentration. Cure speeds increase from 1.6 to 3.3 times for sensitizer concentrations 0.02 to 0.15 percent, respectively, compared to the control sample without EDMA.

EXAMPLE 26

Seven silicone samples were prepared from the vinyl terminated polydimethylsiloxane compound and silicon-bonded hydrogen compound described in Example 1. Two gram mixtures of the said components were prepared such that the amount of hydrosilane compound ranged from 0 to 25.0 weight percent of the total composition.

To each 2 g sample was added 2.0 mg (0.10% by weight) of 9,10-dimethylanthracene sensitizer and 3.0 mg (0.15% by weight) of (Cp)trimethylplatinum hydrosilation catalyst and each sample thoroughly mixed. Gel times for each of the irradiated formulations were measured and recorded in Table V.

TABLE V

| Sample | % Hydrosilane compound | Gel time (seconds) |
|---|---|---|
| 1 | 0 | no cure |
| 2 | 2.5 | 51 |
| 3 | 5.0 | 42 |
| 4 | 10.0 | 35 |
| 5 | 15.0 | 29 |
| 6 | 20.0 | 25 |
| 7 | 25.0 | 22 |

The data of Table V show that the cure speed of the hydrosilation reaction increases with increasing hydrosilane concentration and that in the absence of silicon-bonded hydrogen no polymerization occurs. It was also observed that hydrogen evolution became apparent at high hydrosilane concentration (>15 weight percent).

EXAMPLE 27

A composition (100 g) was prepared by mixing in a glass container 94.90 parts by weight of the vinyl terminated polysiloxane and 5.00 parts by weight of the silicon-bonded hydrogen compound described in Example 1. To each of four 2 g samples was added 3 to 5 mg of one of the four ($\eta^5$-cyclopentadienyl)tri($\sigma$-alphatic)-platinum hydrosilation catalysts listed in Table VI. Each sample was thoroughly mixed, resulting in compositions containing 980 parts of platinum per million parts of total composition. To each sample was added either no sensitizer, 0.05 percent by weight of the sensitizer 9,10-dimethylanthracene (DMA), or 0.05 percent by weight of the sensitizer 2-chlorothioxanthone (CTX).

All of the foregoing compositions were irradiated with a "Visilux" 2 light source according to the method described in Example 1 and gel times were measured and recorded in Table VI.

TABLE IV

| Sample | Platinum catalyst | Sensitizer | Gel time (seconds) |
|---|---|---|---|
| 1 | Cp(trimethylplatinum) | none | 125 |
| 2 | Cp(trimethylplatinum) | DMA$^a$ | 45 |
| 3 | Cp(trimethylplatinum) | CTX$^b$ | 36 |
| 4 | (Methyl-Cp)trimethylplatinum | none | 86 |
| 5 | (Methyl-Cp)trimethylplatinum | DMA | 29 |
| 6 | (Methyl-Cp)trimethylplatinum | CTX | 21 |
| 7 | (Trimethylsilyl-Cp)trimethyl-platinum | none | 67 |
| 8 | (Trimethylsilyl-Cp)trimethyl-platinum | DMA | 32 |
| 9 | (Trimethylsilyl-Cp)trimethyl-platinum | CTX | 32 |
| 10 | (Dimethylphenylsilyl-Cp)trimethyl-platinum | none | 69 |
| 11 | (Dimethylphenylsilyl-Cp)trimethyl-platinum | DMA | 27 |
| 12 | (Dimethylphenylsilyl-Cp)trimethyl-platinum | CTX | 27 |

$^a$9,10-dimethylanthracene
$^b$2-chlorothioxanthone

The data of Table VI show that in all cases the addition of a sensitizer such as 9,10-dimethylanthracene or 2-chlorothioxanthone results in a cure speed enhancement relative to those samples lacking a sensitizer. Gel enhancements range from 1.3 to 4.1 times faster in the presence of a sensitizer.

EXAMPLE 28

This example illustrates the relation between triplet energy and cure time. Visible light curable compositions were prepared by mixing the following ingredients in the amounts indicated:

| Ingredient | Amount (wt. %) |
|---|---|
| Vinyl terminated polymer of Example 1 | 84.87 |
| Cross-linking agent of Example 1 | 14.98 |
| Catalyst (CpPt(CH$_3$)$_3$) | 0.15 |
| Sensitizer | 0.10 |

The sensitizer employed, triplet energy thereof, and cure time of the compositions containing the sensitizer are set forth in Table VII.

TABLE VII

| Sensitizer | Triplet energy (Kcal/mole) | Cure time (sec) |
|---|---|---|
| None | NA | 98 |
| 4-chlorobenzophenone | 68.8 | 63 |
| 4,4'-dimethoxybenzophenone | 68 | 86 |
| triphenylene | 66.5 | 79 |
| 2-chlorothioxanthone | 65 | 19 |
| 1,2-benzanthracene | 47 | 84 |
| 9,10-diphenylanthracene | 42 | 58 |
| 9-vinylanthracene | 42 | 23 |
| azulene | 31 | 69 |
| benz[a]anthracenedione | — | 109 |

Sensitizers having a triplet energy greater than or equal to 31 kcal/mole are effective in the composition of this invention.

EXAMPLE 29

This example illustrates preparation of a dental impression by means of a visible-light curable wash material and a chemically curable tray material.

A visible light curable polyvinylsiloxane formulation was prepared by mixing the following ingredients in the amounts indicated:

| Ingredient | Amount (g) | (wt. %) |
|---|---|---|
| Vinyl terminated polymer of Example 1 | 8.5 | 77.1 |
| Cross-linking agent of Example 1 | 1.5 | 13.6 |
| Catalyst (CpPt(CH$_3$)$_3$) | 0.015 | 0.14 |
| Sensitizer (2-chlorothioxanthone) | 0.01 | 0.10 |
| Fumed silica ("Aerosil R-972") | 1.0 | 9.06 |
|  | 11.025 | 100.00 |

The first four ingredients were premixed; then fumed silica was added. The resultant mixture was painted on the entire surface of a single tooth of a typodont. The coated surface was then irradiated by means of a "Visilux" 2 light over the entire surface for approximately two minutes or until the resin was completely tack-free. Immediately following the irradiation step, a two-part chemically curable impression material (Express Medium Viscosity Wash, Minnesota Mining and Manufacturing Company) was applied by syringe directly over the several teeth both adjacent to and including those previously irradiated with light. The material was allowed to set for about five minutes. The bulk material was easily removed from the typodont by firmly holding the typodont in one hand and the impression in the other. Upon removal of the silicone impression, it was observed that the light-cured material was firmly and completely bonded to the chemically-cured material. The stone model that was prepared from the impression showed improved detail where the light cured material was placed.

Various modifications and alterations of this invention will become apparent to those skilled in the art without departing from the scope and spirit of this invention, and it should be understood that this invention is not to be unduly limited to the illustrated embodiments set forth herein.

What is claimed is:

1. A hydrosilation process which comprises reacting a composition comprising a compound having aliphatic unsaturation and a compound containing at least one silicon-bonded hydrogen atom and not having more than three hydrogen atoms attached to any one silicon atom, in the presence of both a ($\eta^5$-cyclopentadienyl)-tri($\sigma$-aliphatic)platinum complex and a sensitizer that is capable of absorbing visible light and that is capable of transferring energy to said platinum complex such that the hydrosilation reaction is initiated upon exposure to visible light.

2. The process of claim 1 wherein said reaction is carried out by means of exposing said composition to visible radiation.

3. The process of claim 1 wherein said sensitizer has a triplet energy of at least 31 Kcal/mole.

4. The process of claim 1 wherein said sensitizer is a polycyclic aromatic compound.

5. The process of claim 4 wherein said polycyclic aromatic compound has from two to five rings, inclusive.

6. The process of claim 5 wherein said polycyclic aromatic compound is selected from the group consisting of 9,10-dimethylanthracene, 9,10-dichloroanthracene, 2-ethyl-9,10-dimethylanthracene, and azulene.

7. The process of claim 1 wherein said sensitizer is an aromatic compound containing a ketone chromophore.

8. The process of claim 7 wherein said aromatic compound is a thioxanthone.

9. The process of claim 8 wherein said thioxanthone is selected from the group consisting of thioxanthone, 2-chlorothioxanthone, and 2-isopropylthioxanthone.

10. The process of claim 1 wherein the platinum complex has the formula

wherein

Cp represents a cyclopentadienyl group that is eta-bonded to the platinum atom, the cyclopentadienyl group being unsubstituted or substituted by one or more groups that do not interfere in a hydrosilation reaction, and each of $R^1$, $R^2$, and $R^3$ represents an aliphatic group having from one to eighteen carbon atoms, said $R^1$, $R^2$, and $R^3$ groups being sigma-bonded to the platinum atom.

11. The process of claim 10 wherein the platinum complex is selected from the group consisting of:
($\eta^5$-cyclopentadienyl)trimethylplatinum,
($\eta^5$-methylcyclopentadienyl)trimethylplatinum,
($\eta^5$-trimethylsilylcyclopentadienyl)trimethylplatinum, and
($\eta^5$-dimethylphenylsilylcyclopentadienyl)trimethylplatinum.

12. The process of claim 1 wherein the composition comprises from about 0.1 to about 10.0 equivalent weights of the compound having silicon-bonded hydrogen per equivalent weight of the compound having aliphatic unsaturation, and, per 1,000,000 parts by weight of the total composition, from about 5 to about 1000 parts by weight of the platinum catalyst, and from about 50 to about 50,000 parts by weight of the sensitizer.

13. The process of claim 1 wherein the compound containing aliphatic unsaturation is a polyorganosiloxane having the general formula:

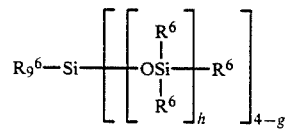

wherein each $R^6$ independently represents a member selected from the group consisting of non-halogenated or halogenated ethylenically-unsaturated groups, non-halogenated or halogenated alkyl groups, non-halogenated or halogenated cycloalkyl groups, and the phenyl group, provided that at least 70% of all $R^6$ groups are methyl groups, but no more than 10% of all $R^6$ groups are vinyl groups or other alkenyl groups, further provided that at least two of the $R^6$ groups are vinyl groups or other alkenyl groups, h is a number having a value from 1 to about 3000, and
g is 0, 1, 2, or 3.

14. The process of claim 1 wherein the compound containing silicon-bonded hydrogen is a polyorganohydrosiloxane having the general formula:

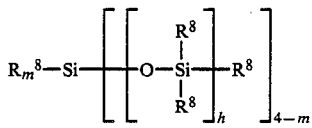

wherein each $R^8$ independently represents a member selected from the group consisting of alkyl groups, cycloalkyl groups, phenyl group, and hydrogen, provided that at least two but no more than one-half of all the $R^8$ groups in the siloxane are hydrogen, m is 0, 1, 2 or 3, and n is a number having an average value from one to about 3000.

15. The process of claim 1 wherein the compound having aliphatic unsaturation is one having olefinic unsaturation.

16. A radiation-curable composition comprising:
(a) a silicon compound containing at least one hydrogen atom attached to silicon per molecule, there being not more than three hydrogen atoms attached to any one silicon atom,
(b) a compound containing aliphatic unsaturation,
(c) a ($\eta^5$-cyclopentadienyl)tri($\sigma$-aliphatic)platinum complex, and
(d) a sensitizer that is capable of absorbing visible light and that is capable of transferring energy to said platinum complex when said composition is exposed to visible light.

17. The composition of claim 16 wherein said sensitizer has a triplet energy of at least 31 Kcal/mole.

18. The composition of claim 16 wherein said sensitizer is a polycyclic aromatic compound.

19. The composition of claim 18 wherein said polycyclic aromatic compound has from two to five rings, inclusive.

20. The composition of claim 19 wherein said polycyclic aromatic compound is selected from the group consisting of 9,10-dimethylanthracene, 9,10-dichloroanthracene, 2-ethyl-9,10-dimethylanthracene, and azulene.

21. The composition of claim 16 wherein said sensitizer is an aromatic compound containing a ketone chromophore.

22. The composition of claim 21 wherein said aromatic compound is a thioxanthone.

23. The composition of claim 22 wherein said thioxanthone is selected from the group consisting of thioxanthone, 2-chlorothioxanthone, and 2-isopropylthioxanthone.

24. The composition of claim 16 wherein the platinum complex is represented by the formula:

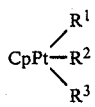

wherein

Cp represents a cyclopentadienyl group that is eta-bonded to the platinum atom, the cyclopentadienyl group being unsubstituted or substituted by one or more groups that do not interfere in a hydrosilation reaction, and each of $R^1$, $R^2$, and $R^3$ represents an aliphatic group having from one to eighteen carbon atoms, said $R^1$, $R^2$, and $R^3$ groups being sigma-bonded to the platinum atom.

25. The composition of claim 24 wherein the platinum complex is selected from the group consisting of:
($\eta^5$-cyclopentadienyl)trimethylplatinum,
($\eta^5$-methylcyclopentadienyl)trimethylplatinum,
($\eta^5$-trimethylsilylcyclopentadienyl)trimethylplatinum, and
($\eta^5$-dimethylphenylsilylcyclopentadienyl)trimethylplatinum.

26. The composition of claim 16, said composition comprising from about 0.1 to about 10.0 equivalent weights of the compound having silicon-bonded hydrogen per equivalent weight of the compound having aliphatic unsaturation, and per 1,000,000 parts by weight of the total composition, from about 5 to about 1000 parts by weight of the platinum complex and from about 50 to about 50,000 parts by weight of the sensitizer.

27. Radiation-curable composition comprising
(a) a polyorganohydrosiloxane having the general formula:

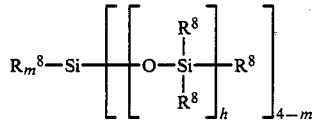

wherein each $R^8$ independently represents a member selected from the group consisting of alkyl groups, cycloalkyl groups, phenyl group, and hydrogen, provided that at least two but no more than one-half of all the $R^8$ groups in the siloxane are hydrogen;

m is 0, 1, 2 or 3, and n is a number having an average value from one to about 3000, (b) a polyorganosiloxane having the general formula:

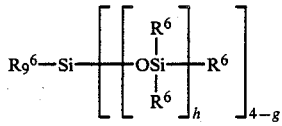

wherein each $R^6$ independently represents a member selected from the group consisting of non-halogenated or halogenated ethylenically unsaturated groups, non-halogenated or halogenated alkyl groups, non-halogenated or halogenated cycloalkyl groups, and the phenyl group, provided that at least 70% of all $R^6$ groups are methyl groups, but no more than 10% of all $R^6$ groups are vinyl groups or other alkenyl groups, further provided that at least two of the $R^6$ groups are vinyl groups or other alkenyl groups, h is a number having a value from 1 to about 3000, and g is 0, 1, 2, or 3, (c) a platinum complex represented by the formula:

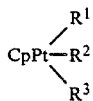

wherein

Cp represents a cyclopentadienyl group that is eta-bonded to the platinum atom, the cyclopentadienyl group being unsubstituted or substituted by one of more groups that are inert in a hydrosilation reaction, and each of $R^1$, $R^2$, and $R^3$ represents an aliphatic group having from one to eighteen carbon atoms, said $R^1$, $R^2$, and $R^3$ groups being sigma-bonded to the platinum atom, and (d) a sensitizer that is capable of absorbing visible light and that is capable of transferring energy to said platinum complex when said composition is exposed to visible light.

* * * * *

UNITED STATES PATENT AND TRADEMARK OFFICE
CERTIFICATE OF CORRECTION

PATENT NO. : 4,916,169

DATED : April 10, 1990

INVENTOR(S) : Boardman et al.

It is certified that error appears in the above-identified patent and that said Letters Patent is hereby corrected as shown below:

Title Page:
In the Abstract, Line 12, after "provides", insert "compositions".

Col. 1, Lines 27-28, after "compound", insert --containing silicon-bonded hydrogen to organic compounds--.

Col. 14, Line 5, "TABLE IV" should read --TABLE VI--.

Col. 16, Line 54, "$R_9^6$" should read --$R_g^6$--.

Col. 17, Line 11, "$_h$" should read --$_n$--.

Col. 18, Line 34, "$_h$" should read --$_n$--.

Col. 18, Line 50, "$R_9^6$" should read --$R_g^6$--.

Signed and Sealed this

Eighth Day of September, 1992

Attest:

DOUGLAS B. COMER

Attesting Officer

Acting Commissioner of Patents and Trademarks